United States Patent

Shipchandler

[11] 4,062,970
[45] Dec. 13, 1977

[54] ZEARALIN ETHERS

[75] Inventor: Mohammed T. Shipchandler, Terre Haute, Ind.

[73] Assignee: IMC Chemical Group, Inc., Terre Haute, Ind.

[21] Appl. No.: 709,694

[22] Filed: July 29, 1976

[51] Int. Cl.$^2$ .................. A61K 31/335; C07D 313/00
[52] U.S. Cl. .............................. 424/279; 260/343.2 F; 260/41
[58] Field of Search .................. 424/279; 260/343.2 F

[56] References Cited

U.S. PATENT DOCUMENTS 3,373,039  3/1968  Hodge et al. ........................ 424/279

Primary Examiner—Frederick E. Waddell
Attorney, Agent, or Firm—E. A. Figg; H. E. Post

[57] ABSTRACT

Novel zearalin ethers are disclosed, which are represented by the formula:

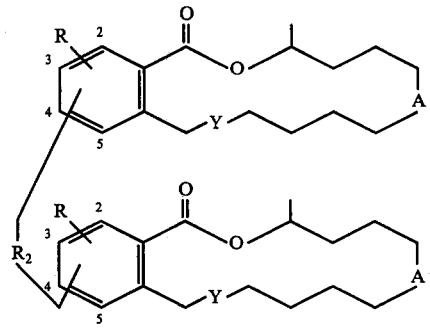

wherein Y may be a single bond or double bond; A may be $-CH_2-$, $>C=O$, or $>CHOR_1$; R represents substituents on each of the aromatic rings in either the 2 or 4 positions and may be H or $OR_1$; $R_1$ may be lower alkyl, lower acyl, monocyclic aryl, or monocyclic aralkyl; $R_2$ represents a substituent common to each of the aromatic rings at either of the 2 or 4 positions which are not substituted by R, and is represented by the formula $-OR_3O-$, wherein $R_3$ is a straight chain or branched chain hydrocarbon; and each aromatic ring may be unsubstituted in the 3 and 5 positions or may be further substituted with one or more halo substituents. Also discosed are methods for making the above compounds, and animal feeds containing such compounds.

8 Claims, No Drawings

ZEARALIN ETHERS

The present invention relates to novel compounds referred to herein as zearalin ethers, to methods for making such compounds, and to animal feeds containing growth promoting amounts of the compounds. More particularly, it relates to compounds of the general formula:

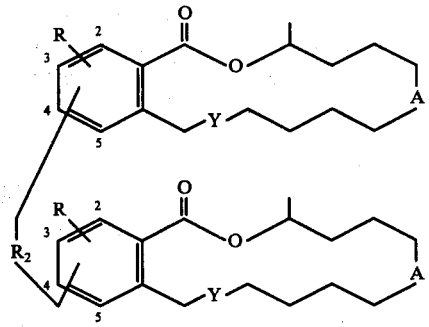

where Y may be a single bond or a double bond; A is selected from the group consisting of —$CH_2$—, >C=O, and >$CHOR_1$; R represents substituents on each of the aromatic rings in either the 2 or 4 positions, and is selected from the group consisting of H and $OR_1$; $R_1$ is selected from the group consisting of lower alkyl of from 1 to about 6 carbon atoms, such as methyl, ethyl, propyl, butyl, pentyl and hexyl, lower acyl of from 1 to about 6 carbon atoms, such as formyl, acetyl, butyroyl, etc., monocyclic aryl of about 6 to 8 carbon atoms, such as phenyl, tolyl, etc., and monocyclic aralkyl, that is, an alkyl group having an aryl substituent thereon, wherein the alkyl group has 1 to about 5 carbon atoms and the aryl group has about 6 to 8 carbon atoms, such as benzyl, tolymethyl, etc.; $R_2$ represents a substituent common to each of the aromatic rings at either of the 2 or 4 positions which are not substituted by R, and is represented by the formula —$OR_3O$—, wherein $R_3$ is a straight chain or branched chain hydrocarbon of from 1 to about 16 carbon atoms such as propyl, butyl, octyl, 3-ethylhexyl, etc.; and each aromatic ring may be unsubstituted in the 3 and 5 positions or may be further substituted with one or more halo, e.g. chloro or bromo, substituents.

As used herein, the term "zearalin" refers to the class of compounds having the basic chemical skeletal formula set forth below, and includes such compounds as zearalenone, zearalanol, etc.

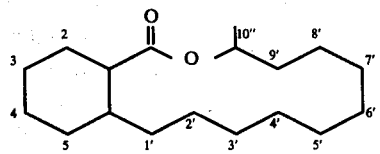

Unless otherwise indicated, the compounds of this invention are not intended to be limited to any particular isomeric configuration, and, more specifically when Y is a double bond, the configuration at that bond may be either cis or trans. The nomenclature used herein generally conforms to that described by Shipchandler, M. T., Heterocycles 3, 471 (1975).

The zearalin ethers of this invention are useful as agents for increasing the rate of growth of meat producing animals, e.g. cattle, lamb, and swine and are particularly advantageous for such use because, in contrast to most other such agents, they possess little or no estrogenic activity, e.g. uterotropic or antigonadotropic.

The compounds can be administered to animals by any suitable method, including oral and parenteral administrations. For example, the compounds can be blended with ordinary feed containing nutritional values in an amount sufficient to produce the desired rate of growth and can thus be fed directly to the animals. Parenteral administration of the compounds may be by injection of a suitable injection suspension medium, such as peanut oil, containing the desired compound, or by subcutaneous implantation of a suitable implant pellet containing such compound.

When a zearalin ether is to be administered in feeds, an animal feed composition may be prepared containing the usual nutritionally-balanced quantities of carbohydrates, proteins, vitamins, and minerals, together with a growth-promoting amount of the zearalin ether. Some of these usual dietary elements are grains, such as ground grain and grain by-products; animal protein substances, such as those found in fish meal and meat scraps; vegetable proteins like soybean oil meal or peanut oil meal; vitaminaceous materials, e.g. vitamin A and D mixtures, riboflavin supplements, and other vitamin B complex members; and bone meal and limestone to provide minerals. A conventional type of feed material for use with cattle includes alfalfa hay and ground corn cobs together with supplementary vitaminaceous substances if desired.

Each of the compounds of the present invention contains two zearalin groups bonded together through a hydrocarbon chain. The zearalin groups may be similar or dissimilar, but compounds having two identical zearalin groups are preferred because of their relative ease of preparation. The zearalins used as starting materials may be prepared from zearalenone, which has the following structure:

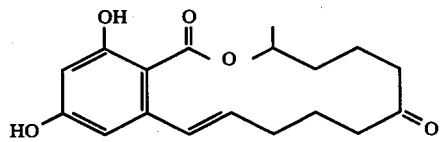

Zearalenone is a natural fermentation product resulting from the cultivation of a zearalenone-producing strain of the microorganism Giberella zeae on a suitable nutrient medium. The production of zearalenone is described in U.S. Pat. No. 3,196,019 issued to Andrews, F. N., et al. on July 20, 1965.

The zearalin ethers are prepared by reacting a zearalin, or a mixture of different zearalins, with a dihaloalkane under etherifying conditions. The particular zearalin used as the starting material depends on the desired end product. Structurally, such zearalins are represented by the formula:

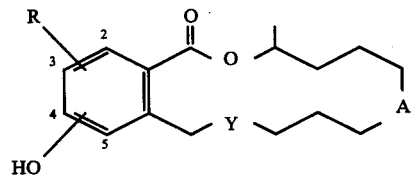

wherein the substituents A, R and Y are defined as in the zearalin ethers above. The preferred starting materials are zearalenone, zearalanone (wherein A is >C=O, Y is a single bond, and the aromatic ring is substituted in the 2 and 4 positions with hydroxyl groups), zearalane (wherein A is —CH$_2$—, Y is a single bond, and the aromatic ring is substituted in the 2 and 4 positions with hydroxyl groups), and zearalanol (wherein A is >CHOH, Y is a single bond, and the aromatic ring is substituted in the 2 and 4 positions with hydroxyl groups).

If a zearalin ether having identical zearalin groups is desired, then a substantially pure zearalin is used as the starting material; however, if a zearalin ether having different zearalin groups is desired, then a mixture of two zearalins having different structures is used as the starting material. The resulting product will include three zearalin ether compounds, one of which will have identical zearalin groups of one structure, one of which will have identical zearalin groups of the other structure, and the third will have the two different zearalin groups. The three different zearalin ethers may be separated, for instance by conventional chromatography techniques, if desired.

The selection of the dihaloalkane for the reaction will depend, in part, upon the length of the hydrocarbon chain through which the zearalin groups of the zearalin ethers are bonded. Generally a hydrocarbon chain of from 1 to about 16 carbon atoms is desired, thus indicating the use of a dihaloalkane having that number of carbon atoms. The preferred dihaloalkane has about 2 to 10 carbon atoms, most preferably about 3 to 6 carbon atoms. The dihaloalkane may have a straight or branched carbon chain, and the halo substituents thereon are preferably bromo or chloro groups. Exemplary of preferred dihaloalkanes are 1,4-dibromobutane, 1,3-dichloropropane, 1,5-dibromopentane, 1,6-dibromohexane, 3-ethyl-1,5-dichloropentane, etc.

The etherifying conditions for the reaction of the zearalin with the dihaloalkane generally include the use of a suitable inert solvent for the reactants. By "inert" is meant a solvent which is substantially non-reactive toward the reactants and products of the reaction. Advantageous solvents include lower aliphatic alcohols of from 1 to about 4 carbon atoms such as methanol, ethanol, etc., and lower aliphatic ketones and amides of from 3 to about 6 carbon atoms, such as acetone, methyl ethyl ketone, dimethylformamide, dimethylacetamide, etc. Methyl ethyl ketone is the preferred solvent for the reaction.

The reaction of a zearalin with a dihaloalkane is essentially a nucleophilic substitution of an alkyl halide with a phenoxide ion. To insure a substantial concentration of phenoxide ions, the reaction mixture preferably includes an inorganic salt of a weaker acid than the phenolic zearalin. Examples of such salts are alkali metal hydroxides, and carbonates, e.g. sodium hydroxide, potassium hydroxide, sodium carbonate, potassium carbonate, etc.

The etherifying conditions also advantageously include an elevated temperature sufficiently high to effect the etherification. Generally, a temperature of from about 20° C to about 200° C, preferably from about 40° C to about 100° C insures substantial etherification. A particularly advantageous method for conducting the reaction at an elevated temperature is by refluxing the reaction mixture.

The concentrations of the reactants are not critical to the formation of the zearalin ether; however, the zearalin and the dihaloalkane are preferably present in the reaction mixture in a substantially stoichiometric ratio, i.e. from about 1.0 to about 3.0, most preferably about 1.5-2.5 moles of zearalin per mole of dihaloalkane. The inorganic salt is preferably present in a molar excess, e.g. from about 2 to about 5, most preferably about 2.2 to about 2.6 moles per mole of dihaloalkane.

The reaction is allowed to proceed for a sufficient time to provide substantial production of the zearalin ether. Generally, a reaction time of from about 1 hour to about 48 hours, preferably about 8 to 15 hours provides substantial production.

The zearalin ether may be recovered from the reaction mixture by any satisfactory means. A convenient method for such recovery is by filtering the mixture while warm to remove the inorganic salts, then cooling the filtrate to effect crystallization of the zearalin ether and separating it by filtration or centrifugation. The product may be further purified, e. g. by recrystallization from methyl ethyl ketone, if desired.

The invention is further illustrated by the following examples, which are not intended to be limiting.

EXAMPLE I

Zearalenone (6.36 g, 20 m mole), 1,4-dibromobutane (2.16 g, 10 m mole), and K$_2$CO$_3$.1½ H$_2$O (4 g, 24 m mole) were dispersed in 100 ml. of methylethyl ketone, and the mixture was refluxed overnight. After refluxing, the reaction mixture was diluted with 40 ml. of methylethyl ketone and filtered while hot. The solid inorganic salts were washed with acetone. The combined filtrate and washings were cooled to room temperature, and 6 g of product was recovered by filtration. The product was recrystallized from methylethyl ketone. The product had a melting range of 179°–180.5° C, and the NMR and IR spectra of the product were consistent with the assigned structure. The following elemental analyses were obtained: Calc. C, 69.54%, H, 7.30%; O, 23.16%; Found C, 69.13%; H, 7.18%; O, 23.32%.

EXAMPLE II

The procedure of Example I was repeated in all essential details, except zearalanol was substituted for zearalenone as the starting material, and the product was recrystallized from chloroform containing a small amount of cyclohexane. The melting range of the resulting product was 162°–163° C and the IR and NMR spectra were consistent with the assigned structure. The following elemental analyses were obtained: Calc. C, 68.74%; H, 8.37%; O, 22.89%; Found C, 68.57%; H, 8.00%; O, 22.72%.

EXAMPLE III

The procedure of Example I is repeated in all essential details, excepts zearalanone is substituted for zearalenone as the starting material, and 2-ethyl-1,4-dibromobutane is substituted for 1,4-dibromobutane. The reaction yields a product of the formula:

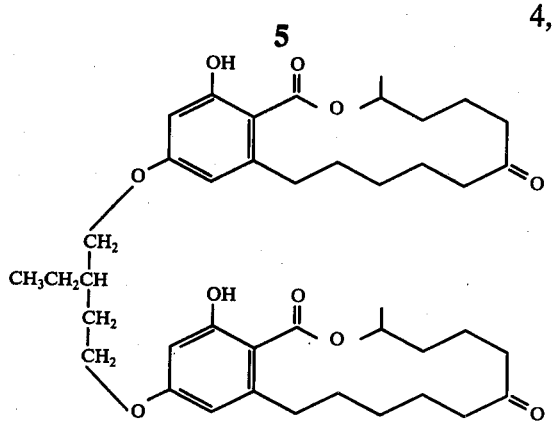
EXAMPLES IV-VI
A series of experiments is conducted in which the procedure of Example I is repeated in all essential details, except, in each experiment, a zearalin starting material as shown in Table I is substituted for zearalenone, and a di-haloalkane as shown in Table I is substituted for 1,4-di-bromobutane. The products of each experiment are also shown in Table I.

TABLE I

| Example No. | Zearalin Starting Material | Dihaloalkane | Product |
|---|---|---|---|
| IV | [structure: methyl ether/hydroxy benzoate macrocycle] | Cl—CH₂CH₂CH₂CH₂CH₂CH₂Cl | [structure: (CH₂)₆-bridged bis-ether product] |
| | | | [structure: (CH₂)₆-bridged bis-ether product, isomer] |
| V | [structure: hydroxy/methoxy zearalenone-type] | $\text{Br—CH}_2\text{—CH(CH}_3\text{)—CH}_2\text{—Br}$ | [structure: CH₂CH(CH₃)CH₂-bridged product] |
| | | | [structure: CH₂CH(CH₃)CH₂-bridged product, isomer] |
| VI | [structure: *φCH₂O / HO benzylated zearalin] | Br—CH₂CH₂CH₂CH₂CH₂Br | [structure: (CH₂)₅-bridged bis-benzyloxy product] |
| | | | [structure: (CH₂)₅-bridged bis-benzyloxy product, isomer] |

\* φCH₂O

\* φ denotes phenyl

EXAMPLES VII AND VIII

Two experiments are conducted in which the procedure of Example I is repeated in all essential details except, in each experiment, equal portions of two different zearalin starting materials, having the structures shown in Table II are substituted for zearalenone, and the dihaloalkane shown in Table II is substituted for 1,4-dibromobutane. Each experiment yields three different zearalin ethers, which are separated by thin-layer chromatography. The desired zearalin ethers, each having two different zearalin groups, are recovered, and the structures are shown in Table II.

TABLE II

| Example No. | Zearalin Starting Material | Dihaloalkane | Product |
|---|---|---|---|
| VII | (structure: dihydroxy benzoate macrocycle with ketone) | Cl—CH$_2$CH$_2$CH$_2$Cl | (structure: bis-zearalin linked by —O—(CH$_2$)$_3$—O—, one with ketone, one with OH) |
| VIII | (structure: methoxycarbonyl/acetate-substituted zearalin with OH) | Br—CH$_2$CH$_2$CH$_2$—Br | (structure: bis-zearalin linked by —O—(CH$_2$)$_3$—O—, dichloro-substituted) |

TABLE II-continued
| Example No. | Zearalin Starting Material | Dihaloalkane | Product |
|---|---|---|---|
| | 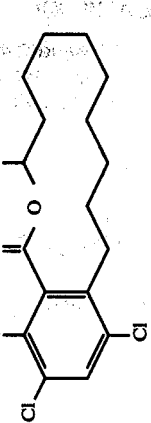 | | |

EXAMPLE IX

The following experiment was conducted to demonstrate the utility, as a growth promoting agent, of a zearalin ether having the following formula (hereinafter sometimes designated Compound A):

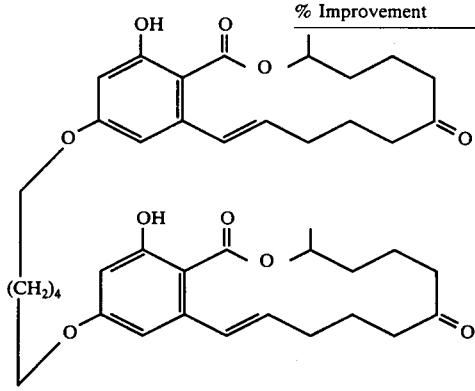

Compound A was administered to lambs by subcutaneous implantation, and its growth promoting activity was compared to a control group of lambs which received no drug.

The compound being tested was formulated into implant pellets for administration to the animals. The implant pellets were prepared by mixing 600 mg. of Compound A with 935 mg. lactose, 52 mg. boric acid, and 24 mg. magnesium stearate, moistening the mixture with aqueous alcohol, and compressing it into pellets, each containing 5.7 mg. of Compound A.

Feeder lambs were blocked by weight within sex, and randomly assigned to treatment. Live weights and feed consumption data were recorded at 14 day intervals for 42 days. During the test, all lambs were self-fed a complete pelleted ration consisting of the following ingredients:

| Ingredients | Amount, lbs. | |
|---|---|---|
| Ground Corn | 790 | |
| Soybean Oil Meal, 44% | 175 | |
| Ground Corn Cobs | 500 | |
| Alfalfa meal, Dehydrated 17% | 400 | |
| Dried Molasses | 100 | |
| Salt | 15 | |
| Premix* | 20 | |
| *Trace Mineral Supplement | 100 | q |
| Vitamin $D_3$ | 1 | g |
| Ground Corn | 20 | lb. |

The lambs were separated into two groups with each group having five ewes and five wethers. During the test, standard management practices, e.g. vaccinations, deworming, watering, bedding, etc., were employed uniformly to all animals. One group of lambs was administered Compound A by subcutaneously implanting two pellets in an ear of each animal. The second group of lambs was used as a control group and was not administered a growth promoting drug.

The results of the test are summarized in Tables III-V. Table III indicates that Compound A significantly improves average daily weight gain over a 42 day period. Table IV indicates that Compound A significantly improves feed efficiency over a 42 day period, and Table V indicates that Compound A does not cause significant teat enlargement.

Table III

| | Average Daily Weight Gain (lbs.) | | | | | | | |
|---|---|---|---|---|---|---|---|---|
| | 0-14 days | | 15-28 days | | 29-42 days | | 0-42 days | |
| Sex | Control | Cpd. A | Control | Cpd. A | Control | Cpd. A | Control | Cpd. A |
| Ewe | .68 | .71 | .57 | .50 | .58 | .75 | .61 | .65 |
| % Improvement | — | 4.4 | — | 0 | — | 29.3 | — | 6.6 |
| Wether | .68 | .94 | .54 | .59 | .81 | .76 | .68 | .76 |
| % Improvement | — | 38.2 | — | 9.3 | — | 0 | — | 11.8 |
| Combined Sex | .68 | .83 | .56 | .55 | .70 | .75 | .64 | .71 |
| % Improvement | — | 22.1 | — | 0 | — | 7.1 | — | 10.9 |

Table IV

| | Ratio of Feed Consumption to Weight Gain | |
|---|---|---|
| Days | Control | Compound A |
| 0-15 | 6.3 | 5.2 |
| % Improvement | — | 21.2 |
| 15-28 | 7.3 | 7.7 |
| % Improvement | — | 0 |
| 29-42 | 6.5 | 6.0 |
| % Improvement | — | 8.3 |
| 0-42 | 6.6 | 6.1 |
| % Improvement | — | 8.2 |

Table V

| | Teat Length* and Diameter* | | | |
|---|---|---|---|---|
| | Length | | Diameter | |
| Sex | Control | Cpd. A | Control | Cpd. A |
| Ewe | 100 | 108 | 113 | 105 |
| % Increase | — | 8.0 | — | 0 |
| Wether | 97 | 102 | 102 | 104 |
| % Increase | — | 5.2 | 0 | 2.0 |

*Table Value = $\dfrac{\text{Sum of final measurement for two tests}}{\text{Sum of initial measurement for two tests}} \times 100$

EXAMPLES X AND XI

The following experiments were conducted to determine the estrogenic activity of compounds having the following structures (herein designated Compound A and Compound B respectively).

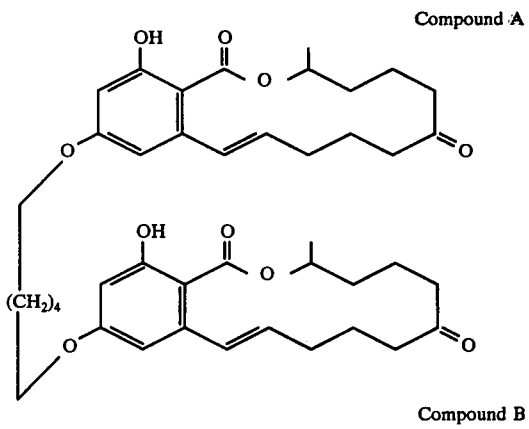

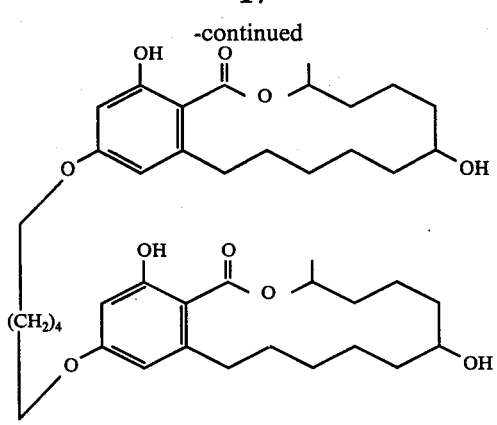

Ovariectomized mice were administered the compounds subcutaneously and orally in a sesame oil diluent over a 3 day period. Control animals were administered sesame oil only, and, for comparison, some animals were administered zearalenone in the same manner as the test compounds. The animals were autopsied on the day following the last administration.

Estrogenicity was determined by comparing the uterine weight (as % of body weight) of the test animals to that of the control animals. The results are summarized in Tables VI and VII. Each result is an average for ten test animals. The data indicate that the compounds possess very little, if any, estrogenic activity.

Table VI

Estrogenicity of Compound B by Oral Administration

| | Total Dose (µg) | Final Body Wt. (g) | Uterine Weight (% B.W.) |
|---|---|---|---|
| Control (sesame oil) | — | 20.5 ± 2.20 | .05483 |
| Compound A | 300 | 22.0 ± 1.69 | .05323 |
| Compound A | 900 | 21.5 ± 1.85 | .06121 |
| Compound A | 2700 | 20.38 ± 1.51 | .05734 |
| Zearalenone | 300 | 20.38 ± 1.77 | .14529 |

Table VII

Estrogenicity of Compound A

| | | Subcutaneous Administration | | Oral Administration | |
|---|---|---|---|---|---|
| | Total Dose (µg) | Final Body Wt. (g) | Uterine Weight (% B.W.) | Final Body Wt. (g) | Uterine Weight (% B.W.) |
| Control (sesame oil) | — | 15.6 ±0.74 | .061 | 22.5 ± 2.07 | .044 |
| Compound A | 150 | 18.0 ± 2.33 | .047 | 20.38 ± 2.20 | .044 |
| Compound A | 300 | 19.13 ± 2.90 | .040 | 20.71 ±0 2.81 | .047 |
| Compound A | 900 | 20.0 ± 2.27 | .048 | 22.38 ± 1.92 | .047 |
| Zearalenone | 300 | 17.5 ± 4.69 | .174 | 21.25 ± 2.55 | .119 |

EXAMPLE XII

The following experiment was conducted to determine the inhibitory effect of Compound A on the secretion of gonadotropins in parabiotic rats. Parabiotic rats, consisting of an intact female and a castrate female were administered Compound A at various dosages. The compound was administered to the castrate member by subcutaneous injection in a sesame oil diluent for 10 successive days. The animals were autopsied on the day following the last administration. The gonadotropin inhibitory effect was determined by measuring the ovarian and uterine weights of the intact member and the uterine weight of the castrate member. The results are summarized in Table VIII. Control animals were administered sesame oil only, and, for comparison purposes, some of the animals were administered zearalenone in the same manner as Compound A. Each result is an average taken for five pairs of animals. The results indicate that Compound A does not possess significant antigonadotropic activity.

Table VIII

| | | Intact Female | | Castrate Female |
|---|---|---|---|---|
| Compound | Daily Dose (µg) | Ovarian wt. (mg) | Uterine wt. (mg) | Uterine wt. (mg) |
| Control (sesame oil) | — | 142.2 | 225.4 | 93.4 |
| Compound A | 50 | 135.1 | 204.7 | 56.9 |
| Compound A | 100 | 113.7 | 162.5 | 65.4 |
| Compound A | 200 | 143.2 | 171.5 | 53.4 |
| Zearalenone | 50 | 36.5 | 141.6 | 99.6 |
| Zearalenone | 100 | 23.4 | 81.2 | 124.2 |

EXAMPLES XIII-XX

A series of experiments is conducted in which the procedure of Example IX is repeated in all essential details except that the products of Examples I-VIII are substituted for the zearalin ether of Example IX. In each experiment, the zearalin ether aids in increasing the rate of growth of the animals.

EXAMPLES XXI-XXVIII

A series of experiments are conducted to demonstrate the growth promoting effects of zearalin ethers in animal feeds. In each experiment, six head of cattle are fed a daily ration of alfalfa hay and ground corn cobs containing from 5 to 20 ounces of a zearalin ether per 100 pounds of feed. Each of the products of Examples II–VIII are tested in this manner, and in each experiment, the rates of growth of the cattle are improved in each experiment.

I claim:
1. A compound having the structural formula

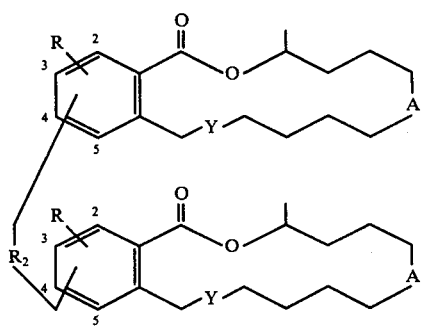

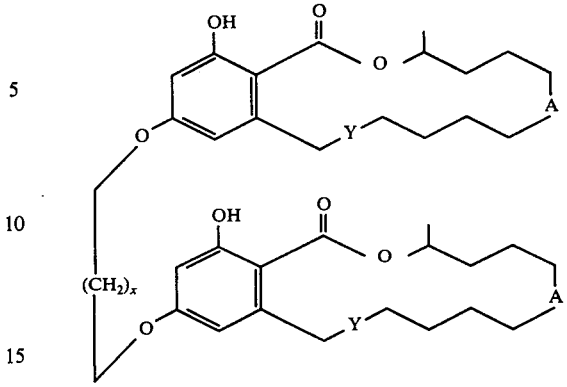

wherein Y may be a single bond or a double bond; A is selected from the group consisting of —CH$_2$—, >C=O, and >CH-OR$_1$; R represents substituents on each of the aromatic rings in either the 2 or 4 positions, and is selected from the group consisting of —H and —OR$_1$; R$_1$ is selected from the group consisting of lower alkyl of from 1 to about 6 carbon atoms, lower acyl of from 1 to about 6 carbon atoms, monocyclic aryl of about 6 to 8 carbon atoms, monocyclic aralkyl in which the alkyl group has 1 to about 5 carbon atoms and the aryl group has about 6 to 8 carbon atoms; R$_2$ represents a substituent common to each of the aromatic rings at either of the 2 or 4 positions which are not substituted by R, and is represented by the formula —OR$_3$O—, wherein R$_3$ is a straight chain or branched chain hydrocarbon of from 1 to about 16 carbon atoms; and the substituents on the 3 and 5 positions are selected from the group consisting of H and halogen atoms.

2. A compound having the structural formula wherein Y may be a single bond or double bond; A is selected from the group consisting of —CH$_2$—, >C=O, and >CHOH; and x is an integer from about 2 to about 10.

3. The compound of claim 2 wherein Y is a double bond, A is >C=O, and x is an integer from about 3 to about 6.

4. The compound of claim 2 wherein Y is a single bond, A is >CHOH, and x is an integer from about 3 to about 6.

5. The compound of claim 2, wherein Y is a single bond, A is >C=O, and x is an integer from about 3 to about 6.

6. The compound of claim 2 wherein Y is a single bond, A is —CH$_2$—, and x is an integer from about 3 to about 6.

7. An animal feed comprising a nutrient ration and a growth promoting amount of the compound of claim 1.

8. An animal feed comprising a nutrient ration and a growth promoting amount of the compound of claim 2.

* * * * *

UNITED STATES PATENT AND TRADEMARK OFFICE
CERTIFICATE OF CORRECTION

PATENT NO. : 4,062,970
DATED : December 13, 1977
INVENTOR(S) : Mohammed T. Shipchandler It is certified that error appears in the above-identified patent and that said Letters Patent are hereby corrected as shown below:

In the Abstract, line 13, "discosed" should read -- disclosed --

Column 1, line 53, 10" should read -- 10' --

Column 4, line 47, "69.13%" should read -- 69.31% --

Column 4, line 64, "excepts" should read -- except --

Column 15, line 58, "100 q" should read -- 100 g --

Signed and Sealed this

Sixteenth Day of May 1978

[SEAL]

Attest:

RUTH C. MASON
Attesting Officer

LUTRELLE F. PARKER
Acting Commissioner of Patents and Trademarks